(12) United States Patent
Martinez et al.

(10) Patent No.: US 8,192,766 B2
(45) Date of Patent: Jun. 5, 2012

(54) COPPER-BASED FUNGICIDE/BACTERICIDE

(75) Inventors: Alfonso Gutierrez Martinez, Chihuahua (MX); Laura Elizabeth Bailon Cisneros, Chihuahua (MX); Pablo Diaz Toledo, Chihuahua (MX); Raul Salazar Franco, Mexico City (MX)

(73) Assignee: Albaugh, Inc., Ankeny, IA (US)

( * ) Notice: Subject to any disclaimer, the term of this patent is extended or adjusted under 35 U.S.C. 154(b) by 0 days.

(21) Appl. No.: 11/410,147

(22) Filed: Apr. 25, 2006

(65) Prior Publication Data
US 2007/0248673 A1 Oct. 25, 2007

(51) Int. Cl.
*A61K 31/74* (2006.01)
*A61K 31/765* (2006.01)
*A61K 33/34* (2006.01)
*A61K 59/20* (2006.01)
*A01N 25/08* (2006.01)

(52) U.S. Cl. .......... 424/630; 424/78.08; 424/78.33; 424/78.1; 424/409; 424/633; 514/772.6

(58) Field of Classification Search ............ 424/78.08, 424/78.33, 78.1, 409, 630, 633; 514/772.6
See application file for complete search history.

(56) References Cited

U.S. PATENT DOCUMENTS

| | | | |
|---|---|---|---|
| 4,020,180 A | 4/1977 | Woerner | |
| 4,075,326 A | 2/1978 | Kuyama et al. | |
| 4,181,786 A | 1/1980 | Mune et al. | |
| 4,409,358 A | 10/1983 | Kraft et al. | |
| 4,418,056 A | 11/1983 | Gonzalez | |
| 4,528,185 A | 7/1985 | Kraft et al. | |
| 4,770,694 A | 9/1988 | Iwasaki et al. | |
| 4,936,901 A | 6/1990 | Surgant, Sr. et al. | |
| 5,298,253 A * | 3/1994 | LeFiles et al. | 424/409 |
| 5,462,738 A * | 10/1995 | LeFiles et al. | 424/409 |
| 6,139,879 A | 10/2000 | Taylor | |
| 6,149,821 A * | 11/2000 | Rounds et al. | 210/754 |
| 6,159,900 A * | 12/2000 | Bieringer et al. | 504/206 |
| 6,436,421 B1 | 8/2002 | Schindler et al. | |
| 6,471,976 B1 | 10/2002 | Taylor et al. | |
| 6,472,347 B1 | 10/2002 | Naguib | |
| 6,562,757 B1 | 5/2003 | Ferrier et al. | |
| 6,689,392 B2 | 2/2004 | Lifshitz | |
| 6,767,865 B2 | 7/2004 | Tandt | |
| 6,849,276 B1 | 2/2005 | Dufau et al. | |
| 6,972,273 B2 * | 12/2005 | Sedun et al. | 504/212 |
| 7,186,887 B2 * | 3/2007 | Kreps et al. | 800/286 |
| 7,238,654 B2 * | 7/2007 | Hodge et al. | 510/199 |
| 2002/0136781 A1 * | 9/2002 | Huato et al. | 424/630 |
| 2006/0057217 A1 * | 3/2006 | Utschig et al. | 424/489 |

FOREIGN PATENT DOCUMENTS

WO   WO 91/13552 A1   9/1991

OTHER PUBLICATIONS

Translation of JP55027164 1, JP date Feb. 27, 1980. translation date Aug. 2011.*
International Search Report for Application No. PCT/US2006/015394; Search completed: Jul. 9, 2007.

* cited by examiner

*Primary Examiner* — Johann Richter
*Assistant Examiner* — Luke Karpinski
(74) *Attorney, Agent, or Firm* — Duane Morris LLP

(57) ABSTRACT

The present invention discloses an improved copper-based fungicide/bactericide composition. The improved composition offers higher biological activity over typical copper-based products, while requiring significantly less copper in the composition. The present invention also discloses methods of making the improved copper-based fungicide/bactericide composition. The present invention further discloses methods of using the improved copper-based fungicide/bactericide composition.

16 Claims, No Drawings

COPPER-BASED FUNGICIDE/BACTERICIDE

BACKGROUND OF THE INVENTION

1. Field of the Invention

The present invention relates generally to fungicides/bactericides. More specifically, the present invention relates to a fungicide/bactericide composition which is based upon a complex of copper and a carboxylic acid derivative, and a method of making and using the fungicide/bactericide composition.

2. Background Art

Fungi are a large group of nongreen plants dependent upon the organic food made by photosynthesizing green plants. They represent a constant and ever present threat to many agricultural crops ranging from tropical and semi-tropical vegetation to temperate climate crops. Thus the control of phytopathogenic fungi is of great economic importance since fungal growth on plants or on parts of plants inhibits production of foliage, fruit or seed, and the overall quality of a cultivated crop. In addition, certain groups of fungi produce mycotoxins in infected crops, directly posing a health hazard to humans and animals. Fungicides are known in the art as either chemical or biological agents used to mitigate, inhibit or destroy fungi. To be economical, the cost of controlling plant diseases must be offset by increased crop yield and quality.

The use of $Cu^{2+}$ ions for protecting crops against phytopathogenic fungi has been known for a long time. As early as 1882, a Bordeaux mixture was used to control the downy mildew on grapes. The Bordeaux mixture consisted of a light blue gelatinous precipitate suspended in water and formed by reacting 4 pounds of copper sulfate with 4 pounds of hydrated lime (calcium hydroxide) in 50 gallons of water. Later, various variations of the Bordeaux mixture have been made by changing the ratio of the components.

Presently, copper based fungicides/bactericides are used extensively in agriculture. It has been observed that various types of copper compounds can be used to effectively treat various plant pathogens, and are available in different types of formulations including wettable powders, emulsifiable concentrates, water-based flowables and dry flowables (also known as water dispersible granules). Dry flowable products are generally dustless, free-flowing, granular products. They are popular among users because the products can be formulated with a higher percentage of active ingredient, are easy to use and have improved shelf life compared to the aqueous fungicides/bactericides. Dry bactericides/fungicides can be stored for a long period of time, over wide extremes of temperature, without destroying the stability of the formulation. Dry bactericides/fungicides formulations also result in lower shipping cost.

While copper compounds have been known for their ability to control fungi/bacteria, the copper materials applied must be relatively non-toxic to the plants. Generally, inorganic copper compounds have been used because they have been observed to be non-phytotoxic, whilst most of the organic copper compounds have been found phytotoxic, especially in foliar applications.

With respect to the inorganic copper compounds, water soluble copper compounds are known to be extremely phytotoxic. As a result, water insoluble copper compounds are used as fungicides/bactericides. However, the low water solubility of the copper compounds presents a different kind of problem.

Biological activity of the copper-based fungicides/bactericides is measured by the free $Cu^{2+}$ ions available for consumption by the fungi or bacteria. The biological activity of a fungicide/bactericide increases with an increase in the amount of free $Cu^{2+}$ ions released. Therefore, the fungicides/bactericides formulated based on water insoluble copper compounds are normally applied in relatively large amounts to effectively control the phytopathogenic fungi. As a result, the relatively high level of copper detracts from cost effectiveness, contributes to soil residue contamination and raises the potential for phytotoxicity.

As an alternative to high level copper compound usage, the water insoluble copper compounds can be milled to fine particle size to increase the surface area of the compounds. The finer the copper compound, the more surface area it can cover with relatively small amounts of copper compounds. However, the methods employed to reduce the particle size of the copper compounds are not always cost effective. In addition, as a practical matter, it is difficult to disperse the finely milled copper compounds because of the tendency of fine particles to agglomerate.

Aside from process and formulation modifications, it is known that a copper complex or copper chelate can be used as a source of free $Cu^{2+}$ instead of water insoluble copper compounds. It has been demonstrated that certain types of copper complexes or chelates are substantially nonphytotoxic and effective fungicides/bactericides for agriculture use.

U.S. Pat. No. 6,139,879 describes an aqueous bactericide/fungicide containing a complex of copper and ethylenediamine-di-o-hydroxyphenylacetic acid (EDDHA).

U.S. Pat. No. 6,471,976 describes an aqueous bactericide/fungicide containing a complex of copper and a partially neutralized polycarboxylic acid. While the bactericides/fungicides reduce the usage of copper compounds, the bioavailable copper from the complexes based on copper hydroxide ranges only from 217 ppm to 3530 ppm (see Table 1 and Table 2).

U.S. Pat. No. 6,562,757 describes a plant-protection composition comprising a copper source in non-chelated form and sparingly soluble calcium, zinc or manganese chelate. Upon application of the composition, copper chelates are formed in situ and gradually released to extend the application interval. U.S. Pat. No. 6,562,757 also describes a process of making the claimed composition by mixing and milling all the dry and powdery ingredients. While the gradual release of $Cu^{2+}$ ions may be advantageous, it is desirable for a fungicide/bactericide to have an effective initial $Cu^{2+}$ ion concentration to provide immediate antifungal/antibacterial effect. It is also desirable to have a process of making a fungicide/bactericide substantially dust-free.

Global health and environment regulations are becoming more and more stringent with respect to unmanaged or unnecessary fungicide/bactericide residues. Farmers around the world are facing a paradox. On one hand, the need to control destructive pathogens requires more fungicide/bactericide use. On the other hand, increasing pressures from regulatory agencies demand less chemical residue on crops and in the soil.

Therefore, a need exists for a copper-based fungicide/bactericide having high biological activity over typical copper-based products, while requiring significantly less copper in the formulation. A need exists for a copper-based fungicide/bactericide having immediate and extended antifungal/antibacterial effect. A need also exists for a process to make and use such fungicide/bactericide cost effectively and environmentally friendly. A way to meet these needs has now been found using the present invention.

SUMMARY OF THE INVENTION

The present invention is directed to an improved copper-based fungicide/bactericide composition. The improved composition offers higher biological activity over typical copper-based products, while requiring significantly less copper in the composition.

The improved copper-based fungicide/bactericide composition of present invention comprises: (a) between about 30.0% to about 90.0% by weight (based on the total weight of all dry ingredients) of a copper compound; (b) between about 0.2% and about 10.0% by weight of a water soluble carboxylic acid derivative; (c) up to about 15.0% by weight of a first dispersant, wherein said first dispersant is selected from the group consisting of a block copolymer non-ionic surfactant having an average molecular weight of between about 1,000 and 15,000, a polycarboxylic acid derivative having a pH of between about 5 and about 10 and an average molecular weight of between about 1,000 and about 37,000, and combinations thereof; (d) between about 0.5% and about 60.0% by weight of a filler; (e) up to about 10.0% by weight of a second dispersant, wherein said second dispersant is selected from the group consisting of lignin sulfonate, naphthalenesulfonate and combinations thereof; and (f) optionally between about 0.01% and about 1.50% by weight of an antifoaming agent, and/or a stabilizer, and/or a wetting agent, and/or combinations thereof.

The present invention is also directed to a method of making the improved copper-based fungicide/bactericide composition. The method comprises: (a) combining between about 30.0% to about 90.0% by weight (based on the total weight of all dry ingredients) of a copper compound wet cake having about 40 to about 60% solid content with, (i) between about 0.2% and about 10.0% by weight of a water soluble carboxylic acid derivative, (ii) up to about 15.0% by weight of a first dispersant, wherein said first dispersant is selected from the group consisting of a block copolymer non-ionic surfactant having an average molecular weight of between about 1,000 and about 15,000, a polycarboxylic acid derivative having a pH of between about 5 and about 10 and an average molecular weight of between about 1,000 and about 37,000, and combinations thereof, (iii) between about 0.5% and about 60.0% by weight of a filler, (iv) up to about 10.0% by weight of a second dispersant, wherein said second dispersant is selected from the group consisting of lignin sulfonate, naphthalenesulfonate and combinations thereof, and (v) optionally an antifoaming agent, and/or a stabilizer, and/or a wetting agent, and/or a combination thereof, (b) mixing to obtain a homogenous slurry; and (c) drying said slurry to a moisture content of less than about 4.0%.

The present invention is further directed to a method of using the improved copper-based fungicide/bactericide composition. The method comprises applying to the plants an effective amount of fungicide/bactericide composition of the invention.

DETAILED DESCRIPTION OF THE DISCLOSED EMBODIMENTS

The present invention relates to an improved copper-based fungicide/bactericide composition and a method of making and using the same. The improved composition offers higher biological activity over typical copper-based products, while requiring significantly less copper in the composition. The decreased copper content reduces the residual fungicide in the soil, and thus reduces the potential for phytotoxicity. The fungicide/bactericide composition of present invention contains a copper complex that is substantially less phytotoxic and more effective against fungi in comparison to typical copper compounds.

More specifically, the improved composition releases and disperses free $Cu^{2+}$ ions up to 10 times more than that of typical copper-based formulations. For example, the present invention releases about 25,000 ppm (parts per million) of $Cu^{2+}$ ions from a copper hydroxide based fungicide/bactericide, compared to about 2,500 ppm of $Cu^{2+}$ ions from typical copper hydroxide based fungicides/bactericides.

A fungicide/bactericide formulation may be produced in accordance with the present invention by mixing between 30.0% to 90.0% by weight (based on the total weight of all dry ingredients) of a copper compound wet cake with, (i) between 0.2% and 10.0% by weight of a water soluble carboxylic acid derivative, (ii) up to about 15.0% by weight of a first dispersant, wherein said first dispersant is selected from the group consisting of a block copolymer non-ionic surfactant having an average molecular weight of between about 1,000 and about 15,000, a polycarboxylic acid derivative having a pH of between about 5 and about 10 and an average molecular weight of between about 1,000 and about 37,000, and the combinations thereof, (iii) between 0.5% and 60.0% by weight of a filler, (iv) up to about 10.0% by weight of a second dispersant, wherein said second dispersant is selected from the group consisting of lignin sulfonate, naphthalenesulfonate and the combinations thereof, and (v) optionally an antifoaming agent, and/or stabilizer, and/or wetting agent and/or the combinations thereof to form a homogeneous aqueous slurry. The slurry is then spray dried in conventional spray drying equipment to obtain dry flowable granules with an average particle size of less than about 8 microns.

The copper compounds useful in the present invention include copper hydroxide, copper oxychloride, tribasic copper sulfate, basic copper carbonate and copper oxide. The preferred copper compounds are copper hydroxide, copper oxychloride and tribasic copper sulfate.

The copper oxychloride wet cake may be produced by mixing metallic copper with hydrochloric acid and water to form copper oxychloride; passing the reaction mixture through a rotary filter to dewater and obtain the copper oxychloride wet cake having about 40-60% solid content, more preferably having about 45-55% solid content, most preferably having about 50% solid content.

The copper hydroxide wet cake may be produced by mixing copper oxychloride with caustic soda to form copper hydroxide; and passing the reaction mixture through a rotary filter to dewater and obtain the copper hydroxide wet cake having about 40-60% solid content, more preferably having about 45-55% solid content, most preferably having about 50% solid content.

The tribasic copper sulfate wet cake may be produced by mixing copper hydroxide with sulfuric acid to form tribasic copper sulfate; and passing the reaction mixture through a rotary filter to dewater and obtain the tribasic copper sulfate wet cake having about 40-60% solid content, more preferably having about 45-55% solid content, most preferably having about 50% solid content.

The water soluble carboxylic acid derivatives useful in the present invention include water soluble metal and ammonium salts of citric acid, malic acid, fumaric acid, succinic acid, glutaric acid, adipic acid, and the like. The preferred water soluble carboxylic acid derivatives are alkali metal salts of citric acid, malic acid, fumaric acid, succinic acid, glutaric acid and adipic acid, and the like. The most preferred water soluble carboxylic acid derivative is sodium citrate available from Jungbunzlauer Austria AG in Pernhofen, Austria.

The block copolymer non-ionic surfactants useful in the present invention include non-ionic surfactants used in emulsifiable and suspension concentrates. Suitable block copolymers are polyalkylene oxide block copolymers having a molecular weight of between about 1,000 to about 15,000. The preferred block copolymer non-ionic surfactant is Toximul® 8323 available from Stephan Company, Illinois, U.S.A.

The polycarboxylic acid derivatives useful in the present invention include polyacrylic acid derivatives. The polyacrylic acid derivatives can be prepared by neutralizing polyacrylic acids having a molecular weight of between about 1,000 and 37,000, preferably between about 5,000 and about 37,000. The polyacrylic acid is neutralized to a pH of between about 5 and about 10 by adding to the polyacrylic acid a neutralizing agent. Suitable neutralizing agents include sodium hydroxide, potassium hydroxide, $NaHCO_3$, $Na_2CO_3$ and the like. The preferred polyacrylic acid derivative is Orotan® 850, available from Rohm and Haas Company, Pennsylvania, U.S.A. Orotan® 850 is a sodium salt of polyacrylic acid.

Other polycarboxylic acid derivatives can also be used in the present invention. Suitable polycarboxylic acids useful in the present invention include polymethacrylic acids; copolymers of acrylic acid and acrylamide, methacrylamide, acrylate esters (methyl, ethyl and butyl), methacrylic acid, methacrylate esters (methyl and ethyl) and maleic anhydride; carboxymethylcellulose; and maleic acid polymers and copolymers with butadiene and maleic anhydride.

The foregoing block copolymer non-ionic surfactants and polycarboxylic acid derivatives may be used alone or in combination to achieve the optimal results.

Fillers for granules, wettable powders, dry flowables of copper-based fungicide/bactericide are known in the art. Suitable fillers include diatomaceous earth, calcium carbonate, calcium bentonite clay and sodium bentonite clay. The preferred diatomaceous earth is available under the trade name Celite 350, having a particle size distribution of $d_{10}$=3.0-3.5 microns, $d_{50}$=10-13 microns and $d_{90}$=20-25 microns. It is available from Celite World Minerals Inc. in California, U.S.A. The preferred calcium carbonate is available under the trade name Carbonato de Calcio extraligero, having a particle size distribution of $d_{10}$=0.5-0.6 microns, $d_{50}$=1.5-1.7 microns and $d_{90}$=8-10 microns. It is available from Qualymin of Monterrey, Mexico.

Lignin sulfonates and naphthalenesulfonates useful as dispersants are known in the art. The preferred lignin sulfonate is available under the trade name Wanin®DP 734 FT, a sodium salt of lignin polymer. It is available from Borregaard Lignotech, Finland. The preferred naphthalenesulfonate is available under the trade name Morwet® D-425, a sodium salt of naphthalene sulfonate condensate. It is available from Akzo Nobel Surface Chemistry LLC, Texas, U.S.A. Lignin sulfonates and naphthalenesulfonates may be used alone or in combination to achieve the optimal results.

The copper based fungicide/bactericide compositions can optionally include other formulation additives, such as wetting agents, antifoam agents and stabilizers. The wetting agents, antifoaming agents and stabilizers are known in the art. The preferred wetting agent is Genapol®X060, a fatty alcohol polyglycol ether non-ionic surfactant, available from Clariant Corporation of Charlotte, N.C., U.S.A. The preferred antifoam agent is AF®365 Antifoam, a polydimethysiloxane antifoam emulsion, available from General Electric of Greenwich, Conn., U.S.A. The preferred stabilizer is glycerol. The wetting agents, antifoam agents and stabilizers can each be incorporated into the compositions in amounts between about 0.01% and about 1.50% by weight (based on the total weight of all dry ingredients). They may be used alone or in combination to achieve the optimal results.

The slurry can be air dried, oven dried or spray dried. Preferably, the slurry is spray dried to form a dry flowable granular product by using a spray dryer equipped with an atomizer. The spray drying chamber has an inlet temperature of about 300° C., and an outlet temperature of about 90° C. The resulting granular product has moisture content of less than about 4.0%, preferably less than about 2.0%. The resulting granular product has an average particle size of less than about 8 microns, preferably less than about 6 microns, more preferably less than about 4 microns.

Using techniques known in the art, the fungicide/bactericide compositions of the present invention can be prepared in other forms, such as flakes, powders, tablets, pellets and solutions.

The fungicide/bactericide compositions are tested for biocopper. The term "biocopper" means free $Cu^{2+}$ ions available for consumption by the fungi or bacteria. The "biocopper" value can be measured by Atomic Absorption Spectrophotometric methods as described below:

a. Preparation of Standard Copper Solutions

Weigh 0.9830 g of copper (II) sulphate (25.4% copper), dissolve in water and dilute to 1000 ml with water to obtain a stock solution. Prepare a working solution from the stock solution by diluting 1:10 with water; take 0, 4.0, 8.0, 12.0 and 20.0 ml portions of this solution and transfer to 100 ml volumetric flasks; add 2 ml of nitric acid and dilute to 100 ml with de-ionized water to obtain standard solutions containing 0, 1, 2, 3, 4 and 5 µg/ml of copper.

b. Preparation of the Calibration Curve

Measure the absorbance of these standards by atomic absorption spectrophotometry in an air-acetylene flame at 324.7 nm and plot the calibration curve of absorption against amount of copper.

c. Determination of Biocopper

Weigh (to the nearest 0.1 mg) a sample (about 0.350 g) and transfer to a 250 ml conical flask, add 100 ml of de-ionized water, stopper tightly and shake vigorously for 1 minute. Allow to stand in a water bath at 20° C. for 1 hour, shake the flask every 15 minutes. Centrifuge about 50 ml of the suspension at 3000 rpm for 20 minutes; filter about 35 ml of the supernatant liquid on a 13 mm Millipore filter; transfer 25 ml of the filtrate to a 50 ml volumetric flask; add 1 ml of concentrated nitric acid and make up to the mark with de-ionized water; mix and measure the absorbance; and read off the concentration of q (µg/ml) of copper from the calibration curve.

d. Calculation $$Biocopper=[q/(50\times W)]\%,$$

wherein W is the sample weight (gram).

The fungicide/bactericide compositions of the present invention may be applied directly to the leaves of a plant at a rate of preferably between about 0.5 and about 12.0 pounds per acre depending on the specific plants to be protected or treated. The fungicide/bactericide compositions of the present invention may also be mixed with water and then sprayed onto the plants using conventional agricultural sprayers and spraying techniques known in the art. The mixing ratio of granulates and water is between about 2:10,000 (w/w) and 5:1,000, more preferably between about 3:10,000 and about 2:1,000, and most preferably 5:10,000. The rate of spray application is preferably between about 10 to 165 gallons per acre depending on the specific plants to be protected or treated.

The fungicide/bactericide compositions of the present invention is useful for treating bacterial and fungal diseases on various plants including citrus, such as grapefruit, lemon, lime, orange, tangelo and tangerine; field crops, such as alfalfa, oats, peanuts, potatoes, sugar beets, wheat, and barley; small fruits, such as blackberry, blueberry, cranberry, currant, gooseberry, raspberry and strawberry; tree crops, such as almond, apple, apricot, avocado, banana, cacao, cherry, coffee, filberts, litchi, mango, nectarine, olive, peach, pear, pecan, plum, pistachio, prune, sugar apple and walnut; vegetables, such as bean, broccoli, brussel sprout, cabbage, cantaloupe, carrot, cauliflower, celery, collards, cucumber, eggplant, honeydew, lettuce, muskmelon, onion, pea, pepper, pumpkin, squash, spinach, tomato, watercress and watermelon; vines, such as grape, hops and kiwi; miscellaneous, such as ginseng, live oak and sycamore and ornamentals, such as *aralia*, azalea, begonia, bulbs (Easter lily, tulip, gladiolus), carnation, chrysanthemum, cotoneaster, Douglass fir, *euonymus*, India hawthorn, ivy, pachysandra, periwinkle, philodendron, *pyracantha*, quince, rose, turfgrass and yucca (Adams-Needle).

The fungicide/bactericide composition of the present invention is useful for treating plants with fungal or bacterial diseases, such as melanose, scab, pink pitting, greasy spot, brown rot, *phytophthora*, citrus canker, *xanthomonas* and cerospora leaf spots, black leaf spot (*alternaria*), alternaria blight, blossom blight, *botrytis* blight, powdery mildew, xanthomonas leaf spot, leaf and cane spot, anthracnose, pseudomonas leaf spot, *septoria* leaf spot, *entomosporium* leaf spot, *volutella* leaf blight, *phomopsis* stem blight, bacterial leaf spot, fire blight, black spot, leaf curl, *coryneum* blight (shot hole), blossom blight, pseudomonas blight (blossom blast), shuck and kernel rot (*Phytophthora cactorum*), zonate leafspot (*Cristulariella pyramidalis*), walnut blight, bacterial blight (halo and common), brown spot, black rot (*xanthomonas*), downy mildew, *cercospora* early blight, septoria late blight, angular leaf spot, phomopsis, purple blotch, bacterial speck, gray leaf mold, septoria leaf spot, dead bud (*Pseudomonas syringae*), *Erwinia herbicola*, *Pseudomonas fluorescens*, stem blight, ball moss, *leptosphaerulina* leaf spots, *helminthosporium* spot blotch, cercospora leaf spot, leaf spot, iron spot, cane spot, fruit rot, blossom brown rot, bacterial blast (*pseudomonas*), European canker, crown or collar rot, sigatoka, black pitting, black pod, coffee berry disease (*Collectotrichum coffeanum*), leaf rust (*Hemileia vastatrix*), iron spot (*Cercospora coffeicola*), pink disease (*Corticium salmonicolor*) eastern filbert blight, and peacock spot.

The following examples are illustrative of the present invention and are not intended to limit the scope of the invention as set forth in the appended claims.

Example 1

The following ingredients are combined and mixed together to form a substantially homogeneous slurry:

TABLE 1

| Ingredients | Pounds |
| --- | --- |
| Copper hydroxide wet cake (50% solid content) | 4354.0 |
| Sodium citrate | 205.5 |
| Toximul 8323 | 141.0 |
| Orotan 850 | 308.3 |
| Diatomaceous earth | 67.0 |
| Naphthalenesulfonate | 257.0 |
| GenapolX060 | 51.0 |
| AF 365 Antifoam | 11.0 |
| Glycerol | 51.0 |

Pump a calculated amount of copper hydroxide wet cake (50% solid content) into a formulation tank and add all ingredients in Table 1. Allow a five-minute waiting period between each addition to ensure good dissolution and dispersion of added ingredients. The resulting slurry is then pumped to a spray dryer feed tank to be spray dried to dry flowable granular products. The spray dryer is equipped with an atomizer, and has an inlet chamber temperature of about 300° C. and an outlet temperature of about 90° C. The dry granular products are collected and packaged, having moisture content of less than about 2.0%.

Example 2

The granules are made as in Example 1 and are measured for biocopper:

TABLE 2

| Ingredients | Formulation A Wt %* | Formulation B Wt %* | Formulation C Wt %* |
| --- | --- | --- | --- |
| Tribasic copper sulphate | 96.70 | 73.30 | 65.70 |
| Sodium citrate | — | 1.50 | 1.50 |
| Toximul 8323 | — | 3.00 | 3.00 |
| Diatomaceous earth | — | 7.10 | 10.90 |
| Calcium carbonate | — | 7.10 | 10.90 |
| Sodium lignosulfonate | 2.80 | 7.00 | 7.00 |
| Genapol X060 | 0.50 | 0.50 | 0.50 |
| AF 365 Antifoam | — | 0.50 | 0.50 |
| Biocopper | 1,765 ppm | 10,000 ppm | 9,100 ppm |

*Wt % is based on the total weight of all dry ingredients.

Example 3

The granules are made as in Example 1 and are measured for biocopper:

TABLE 3

| Ingredients | Formulation A Wt %* | Formulation B Wt %* | Formulation C Wt %* |
| --- | --- | --- | --- |
| Copper oxychloride | 85.75 | 43.4 | 36.9 |
| Sodium citrate | — | 1.00 | 1.00 |
| Diatomaceous earth | 6.75 | 21.00 | 21.00 |
| Calcium carbonate | — | 25.40 | 31.90 |
| Sodium lignosulfonate | 7.00 | 8.00 | 8.00 |
| Genapol X060 | 0.50 | 1.00 | 1.00 |
| AF 365 Antifoam | — | 0.20 | 0.20 |
| Biocopper | 1,100 ppm | 27,000 ppm | 26,000 ppm |

*Wt % is based on the total weight of all dry ingredients.

As can be seen from Tables 2 and 3, the fungicide/bactericide compositions containing water soluble carboxylic acid derivatives, such as sodium citrate in examples 2 and 3, have significantly higher biocopper content while having less copper.

Example 4

The granules are made as in Example 1 and are measured for biocopper:

TABLE 4

| Ingredients | Formulation A Wt %* | Formulation B Wt %* | Formulation C Wt %* |
| --- | --- | --- | --- |
| Copper oxychloride | 88.25 | 85.43 | 85.75 |
| Sodium citrate | 4.00 | 5.00 | — |
| Orotan 850 | 6.00 | — | — |
| Diatomaceous earth | 0.75 | 2.57 | 6.75 |
| Sodium lignosulfonate | — | 6.00 | 7.00 |
| Genapol X060 | 1.00 | 1.00 | 0.50 |
| Biocopper | 25,000 ppm | 27,000 ppm | 1,100 ppm |

*Wt % is based on the total weight of all dry ingredients.

Example 5

The granules are made as in Example 1 and are measured for biocopper:

TABLE 5

| Ingredients | Formulation A Wt %* | Formulation B Wt %* | Formulation C Wt %* | Formulation D Wt %* |
|---|---|---|---|---|
| Copper hydroxide | 41.78 | 37.28 | 84.55 | 84.55 |
| Sodium citrate | — | 4.50 | — | 4.00 |
| Toximul 8323 | 4.00 | 4.00 | 2.75 | 2.75 |
| Orotan 850 | 6.00 | 6.00 | — | — |
| Diatomaceous earth | 9.00 | 9.00 | 5.50 | 1.50 |
| Calcium carbonate | 37.14 | 37.14 | — | — |
| Naphthalenesulfonate | 5.00 | 5.00 | 5.00 | 5.00 |
| Genapol X060 | 1.00 | 1.00 | 1.00 | 1.00 |
| AF 365 Antifoam | 0.08 | 0.08 | 0.20 | 0.20 |
| Glycerol | 1.00 | 1.00 | 1.00 | 1.00 |
| Biocopper | 6,000 ppm | 30,000 ppm | 5,500 ppm | 19,000 ppm |

*Wt % is based on the total weight of all dry ingredients.

As can be seen from Table 5, the fungicide/bactericide compositions containing water soluble carboxylic acid derivatives, such as sodium citrate, have significantly higher biocopper content (comparing formulation A to B, or comparing formulation C to D). Also, the carboxylic acid derivative and the first dispersants exhibit a synergistic effect on the biocopper content (comparing formulation B to D). More specifically, by using an effective amount of a carboxylic acid derivative, such as sodium citrate, together with an effective amount of a first dispersant, such as a combination of block copolymer non-ionic surfactant and a polyacrylic acid derivative, the fungicide/bactericide composition exhibits significantly higher biocopper content (30,000 ppm vs. 19,000 ppm) while requiring much less copper (37.28% vs. 84.55%).

Example 6

The granules A, B, C, D, E, F, G, H, I, J, K, L, M, N and Ň are made as in Example I and are measured for biocopper:

TABLE 6

| Ingredients | Formulation A | B | C | D | E | F | G | H |
|---|---|---|---|---|---|---|---|---|
| Copper Hydroxide | 84.74% | 84.74% | 84.74% | 84.74% | 84.74% | 84.74% | 84.74% | 84.74% |
| Carboxylic acid derivatives | 4.50% | 4.50% | 4.50% | 4.50% | 4.50% | 6.00% | 6.00% | 6.00% |
| Glycerol | 1.00% | 1.00% | 1.00% | 1.00% | 1.00% | 1.00% | 1.00% | 1.00% |
| Wetting agent | 1.00% | 1.00% | 1.00% | 1.00% | 1.00% | 0.25% | 0.25% | 0.25% |
| Antifoaming agent | 0.02% | 0.02% | 0.02% | 0.50% | 0.50% | 0.02% | 0.02% | 0.02% |
| Diatomaceous earth | 0.74% | 2.74% | — | 0.26% | — | 2.99% | 0.99% | 0.24% |
| Block copolymer non-ionic surfactant | 2.00% | — | 2.00% | 4.00% | 4.00% | 2.00% | 4.00% | 2.75% |
| Naphtalensulfonate | — | — | — | — | — | — | — | 5.00% |
| Calcium carbonate | — | — | 0.74% | — | 0.26% | — | — | — |
| Polyacrylic acid derivatives (molecular weight 5,000 Mw) | — | — | — | — | — | 3.00% | — | — |
| Polyacrylic acid derivatives (molecular weight 5,500 Mw) | — | — | — | — | — | — | 3.00% | — |
| Polyacrylic acid derivatives (molecular weight 30,000 Mw) | 6.00% | 6.00% | 6.00% | 4.00% | 4.00% | — | — | — |
| Biocopper (ppm) | 23,900 | 24,500 | 24,300 | 23,400 | 25,000 | 28,500 | 29,200 | 28,600 |

| Ingredients | Formulation I | J | K | L | M | N | Ň |
|---|---|---|---|---|---|---|---|
| Copper Hydroxide | 84.74% | 84.74% | 84.74% | 84.74% | 84.74% | 84.74% | 83.74% |
| Carboxylic acid derivatives | 6.00% | 6.00% | 6.00% | 6.00% | 6.00% | 6.00% | 6.00% |
| Glycerol | 1.00% | 1.00% | 1.00% | 1.00% | 1.00% | 1.00% | 1.00% |
| Wetting agent | 0.25% | 0.25% | 0.25% | 0.25% | 0.25% | 0.25% | 0.25% |
| Antifoaming agent | 0.02% | 0.02% | 0.02% | 0.02% | 0.02% | 0.02% | 0.02% |
| Diatomaceous earth | 0.99% | 0.99% | 0.24% | 1.99% | 1.99% | 0.10% | 0.10% |
| Block copolymer non-ionic surfactant | 4.00% | 4.00% | 2.75% | 3.00% | 3.00% | 4.00% | 3.00% |
| Naphtalensulfonate | — | — | 5.00% | — | — | — | — |
| Calcium carbonate | — | — | — | — | — | 0.89% | 0.89% |
| Polyacrylic acid derivatives (molecular weight 5,000 Mw) | — | 3.00% | — | 3.00% | — | — | — |
| Polyacrylic acid derivatives (molecular weight 5,500 Mw) | 3.00% | — | — | — | 3.00% | — | — |
| Polyacrylic acid derivatives (molecular weight 30,000 Mw) | — | — | — | — | — | 3.00% | 5.00% |
| Biocopper (ppm) | 28,700 | 28,000 | 28,600 | 29,700 | 29,600 | 29,000 | 30,000 |

Example 7

The granules A1, B1, C1, D1, E1, F1, G1, H1, I1 and J1 are made as in Example 1 and are measured for biocopper:

TABLE 7

| Ingredients | Formulations | | | | |
|---|---|---|---|---|---|
| | A1 | B1 | C1 | D1 | E1 |
| Copper Hydroxide | 38.33% | 38.33% | 38.33% | 38.33% | 38.33% |
| Carboxylic acid derivatives | 6.00% | 2.50% | 2.50% | 2.50% | 2.50% |
| Glycerol | 1.00% | 1.00% | 1.00% | 1.00% | 1.00% |
| Wetting agent | 0.25% | 0.25% | 0.25% | 0.25% | 0.25% |
| Antifoaming agent | 0.02% | 0.02% | 0.02% | 0.02% | 0.02% |
| Diatomaceous earth | 45.40% | 49.92% | 55.90% | 52.90% | 52.90% |
| Block copolymer non-ionic surfactant | 3.00% | — | — | — | — |
| Naphtalensulfonate | 6.00% | — | — | — | — |
| Calcium carbonate | — | — | — | — | — |
| Polyacrylic acid derivatives (molecular weight 1,000 Mw) | — | — | — | — | 5.00% |
| Polyacrylic acid derivatives (molecular weight 5,000 Mw) | — | — | — | 5.00% | — |
| Polyacrylic acid derivatives (molecular weight 5,000 Mw) | — | — | — | — | — |
| Polyacrylic acid derivatives (molecular weight 1,0000 Mw) | — | — | 2.00% | — | — |
| Polyacrylic acid derivates (molecular weight 11,000 Mw) | — | 6.00% | — | — | — |
| Polyacrylic acid derivates (molecular weight 30,000 Mw) | — | — | — | — | — |
| Polyacrylic acid derivates (molecular weight 18,000 Mw) | — | — | — | — | — |
| Calcium bentonite clay | — | — | — | — | — |
| Sodium bentonite clay | — | — | — | — | — |
| Lignosulfonates | — | — | — | — | — |
| Biocopper (ppm) | 24,200 | 22,800 | 11,200 | 11,500 | 10,000 |

| Ingredients | Formulations | | | | |
|---|---|---|---|---|---|
| | F1 | G1 | H1 | I1 | J1 |
| Copper Hydroxide | 38.33% | 38.33% | 42.37% | 38.33% | 38.33% |
| Carboxylic acid derivatives | 2.50% | 4.50% | 4.50% | 5.00% | 5.00% |
| Glycerol | 1.00% | 1.00% | 1.00% | 1.00% | 1.00% |
| Wetting agent | 0.25% | 1.00% | 1.00% | 0.25% | 0.25% |
| Antifoaming agent | 0.02% | 0.50% | 0.50% | 0.50% | 0.50% |
| Diatomaceous earth | 52.90% | 0.80% | 4.50% | 4.50% | 4.50% |
| Block copolymer non-ionic surfactant | — | 4.00% | 4.00% | 2.50% | 3.00% |
| Naphtalensulfonate | — | — | — | 5.00% | 5.00% |
| Calcium carbonate | — | 43.87% | 36.13% | 39.90% | 39.42% |
| Polyacrylic acid derivatives (molecular weight 1,000 Mw) | — | — | — | — | — |
| Polyacrylic acid derivatives (molecular weight 5,000 Mw) | — | — | — | — | — |
| Polyacrylic acid derivatives (molecular weight 5,000 Mw) | — | — | — | — | — |
| Polyacrylic acid derivatives (molecular weight 1,0000 Mw) | — | — | — | — | — |
| Polyacrylic acid derivates (molecular weight 11,000 Mw) | — | — | — | — | — |
| Polyacrylic acid derivates (molecular weight 30,000 Mw) | — | 6.00% | 6.00% | — | — |
| Polyacrylic acid derivates (molecular weight 18,000 Mw) | 5.00% | — | — | — | — |
| Calcium bentonite clay | — | — | — | — | — |
| Sodium bentonite clay | — | — | — | — | — |
| Lignosulfonates | — | — | — | 3.00% | 3.00% |
| Biocopper (ppm) | 11,500 | 25,900 | 25,000 | 28,000 | 27,900 |

Example 8

The granules K1, L1, M1, N1, Ň1, O, P, Q, R and S are made as in Example 1 and are measured for biocopper:

TABLE 8

| Ingredients | K1 | L1 | M1 | N1 | Ň1 |
|---|---|---|---|---|---|
| Copper Hydroxide | 38.33% | 38.33% | 42.37% | 42.37% | 42.37% |
| Carboxylic acid derivates | 5.00% | 5.00% | 4.50% | 4.50% | 6.00% |
| Glycerol | 1.00% | 1.00% | 1.00% | 1.00% | 1.00% |
| Wetting agent | 0.25% | 0.25% | 0.25% | 0.25% | 0.25% |
| Antifoaming agent | 0.50% | 0.50% | 0.50% | 0.50% | 0.50% |
| Diatomaceous earth | 4.50% | 43.92% | 4.50% | 4.50% | 44.88% |
| Block copolymer non-ionic surfactant | 3.00% | 3.00% | 4.00% | 4.00% | 2.00% |
| Naphtalensulfonate | 5.00% | 5.00% | 5.00% | 5.00% | — |
| Calcium carbonate | 38.42% | — | 37.88% | 34.88% | — |
| Polyacrylic acid derivates (molecular weight 5,000 Mw) | — | — | — | — | 3.00% |
| Polyacrylic acid derivates (molecular weight 5,500 Mw) | — | — | — | — | — |
| Polyacrylic acid derivates (molecular weight 3,0000 Mw) | — | — | — | — | — |
| Calcium bentonite clay | — | — | — | — | — |
| Sodium bentonite clay | — | — | — | — | — |
| Lignosulfonates | 4.00% | 3.00% | — | 3.00% | — |
| Biocopper (ppm) | 27,000 | 26,900 | 24,500 | 23,000 | 29,000 |

| Ingredients | O | P | Q | R | S |
|---|---|---|---|---|---|
| Copper Hydroxide | 42.37% | 42.37% | 42.37% | 38.33% | 42.37% |
| Carboxylic acid derivates | 6.00% | 6.00% | 6.00% | 4.50% | 4.50% |
| Glycerol | 1.00% | 1.00% | 1.00% | 1.00% | 1.00% |
| Wetting agent | 0.25% | 0.25% | 0.25% | 0.25% | 0.25% |
| Antifoaming agent | 0.50% | 0.50% | 0.50% | 0.50% | 0.50% |
| Diatomaceous earth | 44.88% | — | — | — | — |
| Block copolymer non-ionic surfactant | 2.00% | 4.00% | 4.00% | 4.00% | 4.00% |
| Naphtalensulfonate | — | — | — | — | — |
| Calcium carbonate | — | 42.88% | 42.88% | — | — |
| Polyacrylic acid derivates (molecular weight 5,000 Mw) | — | 3.00% | — | — | — |
| Polyacrylic acid derivates (molecular weight 5,500 Mw) | 3.00% | — | 3.00% | — | — |
| Polyacrylic acid derivates (molecular weight 3,0000 Mw) | — | — | — | 6.00% | 6.00% |
| Calcium bentonite clay | — | — | — | 40.92% | 36.88% |
| Sodium bentonite clay | — | — | — | 4.50% | 4.50% |
| Lignosulfonates | — | — | — | — | — |
| Biocopper (ppm) | 30,000 | 28,700 | 27,200 | 26,000 | 27,500 |

What is claimed is:

1. A fungicide/bactericide composition consisting essentially of:
   (a) a complex of copper and a citric acid derivative, in which the ratio of copper and citric acid is between 1:0.02 and 1:0.16 based on the weight of copper compound and citric acid derivative;
   (c) a first dispersant, wherein said first dispersant is selected from the group consisting of a block copolymer non-ionic surfactant having an average molecular weight of between 1,000 and 15,000, a polyacrylic acid derivative having a pH of between 5 and 10 and an average molecular weight of between 1,000 and 37,000, and combinations thereof; and
   (e) a second dispersant, wherein said second dispersant is selected from the group consisting of lignin sulfonate, naphthalene sulfonate and combinations thereof.

2. The composition of claim 1 wherein said citric acid derivative is sodium citrate.

3. The composition of claim 1, wherein said complex is formed by the contact of said citric acid derivative with a copper compound selected from the group consisting of copper hydroxide, copper oxychloride, tribasic copper sulfate, basic copper carbonate and copper oxide.

4. The composition of claim 2, wherein said complex is formed by the contact of sodium citrate with a copper compound selected from the group consisting of copper hydroxide, copper oxychloride, tribasic copper sulfate, basic copper carbonate and copper oxide.

5. The composition of claim 1, wherein said complex is formed by the contact of said citric acid derivative with copper hydroxide.

6. The composition of claim 2, wherein said complex is formed by the contact of sodium citrate with copper hydroxide.

7. The composition of claim 6, wherein said first dispersant is a block copolymer non-ionic surfactant having an average molecular weight of between 1,000 and 15,000.

8. The composition of claim 6, wherein said first dispersant is a sodium salt of polyacrylic acid.

9. The composition of claim 8, wherein said first dispersant is a sodium salt of polyacrylic acid having a pH of between 9 and 10.8.

10. The composition of claim 6, wherein said first dispersant is a combination of a block copolymer non-ionic surfactant having an average molecular weight of between 1,000 and 15,000 and a sodium salt of polyacrylic acid having a pH of between 9 and 10.8.

11. The composition of claim 6, wherein said second dispersant is naphthalene sulfonate.

12. The composition of claim 11, wherein said second dispersant is a sodium salt of naphthalene sulfonate.

13. The composition of claim 6, further comprising a wetting agent, an antifoam agent and a stabilizer.

14. The composition of claim 13, wherein said wetting agent is a fatty alcohol polyglycol non-ionic surfactant.

15. The composition of claim 13, wherein said antifoam agent is a polydimethylsiloxane antifoam emulsion.

16. The composition of claim 1, consisting essentially of the following ingredients: copper hydroxide, sodium citrate, a block copolymer non-ionic surfactant having an average molecular weight of between 1,000 and 15,000, a sodium salt of polyacrylic acid having a pH of between 9 and 10.8, diatomaceous earth, calcium carbonate, naphthalene sulfonate, a fatty alcohol polyglycol non-ionic surfactant, a polydimethylsiloxane antifoam emulsion and glycerol.

* * * * *